United States Patent [19]

Rautenstrauch

[11] 4,088,664

[45] May 9, 1978

[54] PROCESS FOR THE PREPARATION OF ALKYL γ, δ-UNSATURATED CARBOXYLATES

[75] Inventor: Valentin Rautenstrauch, Grand-Lancy, Switzerland

[73] Assignee: Firmenich S.A., Geneva, Switzerland

[21] Appl. No.: 753,524

[22] Filed: Dec. 22, 1976

[30] Foreign Application Priority Data

Dec. 23, 1975 Switzerland ............... 16675/75
Jun. 4, 1976 Switzerland ............... 7104/76

[51] Int. Cl.$^2$ ............................................ C11C 3/02
[52] U.S. Cl. ............................... 260/410.9 R; 560/122
[58] Field of Search ............... 260/410.9 R, 410.9 M, 260/410.9 A, 468 L; 252/522; 560/122

[56] References Cited

U.S. PATENT DOCUMENTS

| 3,928,403 | 12/1975 | Fujita et al. ............ 260/410.9 R |
| 3,937,723 | 2/1976 | Schulte-Elte ............ 252/522 X |
| 3,963,675 | 6/1976 | Naegli ............ 560/122 |

*Primary Examiner*—Winston A. Douglas
*Assistant Examiner*—John F. Niebling
*Attorney, Agent, or Firm*—Pennie & Edmonds

[57] ABSTRACT

Process for the preparation of γ,δ-unsaturated carboxylate esters which comprises reacting an α,β-unsaturated alcohol with a trialkyl orthopropionate in the presence of an organic acid having $pk_2$ of about 7 to 9.

Among the thus obtained γ,δ-unsaturated carboxylate esters, 2,5,9-trimethyl-deca-3,4,8-triene-carboxylates and 2-methyl-3-[2-methyl-5-isopropenyl-cyclopent-1-en-1-yl]-propionates are particularly useful as intermediates for the preparation of perfuming ingredients.

4 Claims, No Drawings

PROCESS FOR THE PREPARATION OF ALKYL γ, δ-UNSATURATED CARBOXYLATES

BACKGROUND OF THE INVENTION

2-Methyl-3-[2-methyl-5-isopropenyl-cyclopent-1en-1-yl]-propyl ester derivatives are compounds of particular interest for perfumery, see U.S. Pat. Nos. 3,937,723 and 3,978,009. They develop a variety of odoriferous notes ranging from green to fruity or flowery notes and, accordingly, they find a very broad field of use in various fine and technical perfume compositions.

A process for their preparation - see above cited U.S. patents - consists in thermally cyclising 2,6-dimethyl-oct-2-en-7-yn-6-ol, treating the thus obtained product with ethyoxyprop-1-ene to yield an aldehydic derivative, reducing the obtained aldehyde to the corresponding primary alcohol and eventually acylating the said alcohol. The said process is illustrated by the herinbelow reaction scheme.

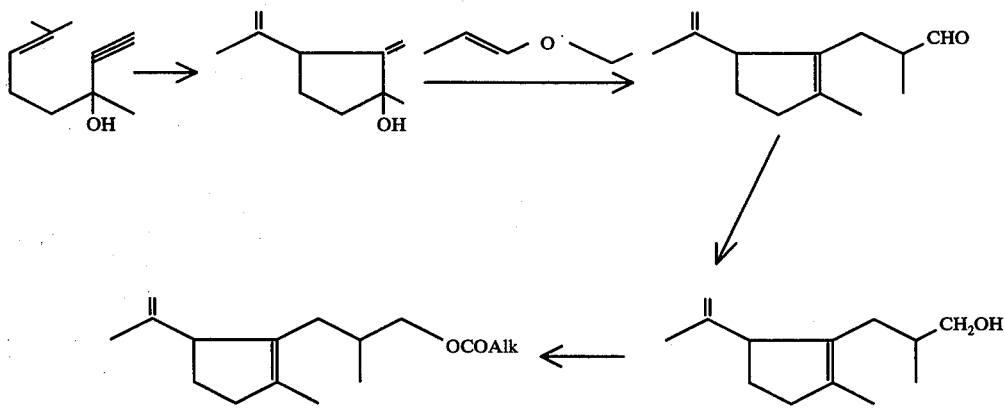

Alk = alkyl radical

The above said process, which sofar has been successfully applied to industrial scale preparations, suffers however of certain practical disadvantages. The reaction between the cyclic tertiary alcohol and ethoxyprop-1-ene, in fact, is very often accompanied by concomitant polymerizations, which consequently reduce the yields of the end-product and increase the technical difficulty in the final purification step. A novel, more satisfactory approach for the preparation of the aforementioned ester derivatives was therefore the goal of further investigations.

THE INVENTION

We have now discovered that 2-methyl-3-[2-methyl-5-isopropenyl-cyclopent-1-en-1-yl]-propyl carboxylates of formula

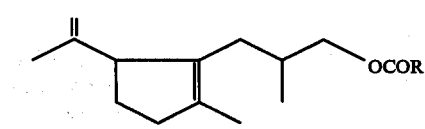

(I)

wherein symbol R represents a lower alkyl radical comprising from 1 to 6 carbon atoms, can be prepared by an original process which comprises:
(a) treating 1-methyl-2-methylene-3-isopropenyl-cyclopentanol with a trialkyl ortho-propionate in the presence of an organic acid having a $pk_a$ of about 7 to 9, to yield an alkyl 2-methyl-3-[2-methyl-5-isopropenyl-cyclopent-1-en-1-yl]-propionate,
(b) reducing the thus obtained ester to the corresponding primary alcohol, and
(c) esterifying the said alcohol to give the desired carboxylate of formula (I).

This invention relates further to a process for the preparation of the carboxylates of formula (I) which consists in
(i) treating 2,6-dimethyl-oct-2-en-7-yn-6-ol with a trialkyl ortho-propionate in the presence of an organic acid having a $pk_a$ of about 7 to 9, to yield an alkyl 2,5,9-trimethyl-deca-3,4,8-triene-carboxylate,
(ii) reducing the thus obtained ester to the corresponding allenic primary alcohol,
(iii) thermally cyclizing the said allenic alcohol to give 2-methyl-3-[2-methyl-5-isopropenyl-cyclopent-1-en-1-yl]-propanol, and finally
(iv) esterifying the said alcohol to give the desired carboxylate.

According to a variante of the hereinabove process, the allenic primary alcohol obtained according to ii) is:
(iii') esterified to give a 2,5,9-trimethyl-deca-3,4,8-trien-1-yl carboxylate which is then
(iv') thermally cyclized to give a 2-methyl-3-[2-methyl-5-isopropenyl-cyclopent-1-en-1-yl]-propyl carboxylate of formula (I).

The key steps in the above given reaction sequences is represented by reactions (a) and (i), respectively, which, formally, constitute examples of rearrangements of the "Claisen" type. This type of rearrangement has been observed in particular in the conversion of secondary allylic alcohols into their corresponding γ,δ-unsaturated esters - see e.g.: J. Amer. Chem. Soc., 92, 741, (1970)-. On the other hand, the reports published in the scientific literature show that the several attempts carried out on tertiary allylic alcohols are far from encouraging practical application of the said Claisen rearrangement for preparing the corresponding γ,δ-unsaturated esters, [see, e.g.: Chemistry Letters, 1974, 741; Angew, Chem., 87, 109 (1975); Comp. Rend. Acad. Sci., Paris, Ser. B, 273, 1382 (1971); Chem. Comm., 1970, 1411; J. Org. Chem., 38, 894 (1973); J. Chem. Soc., Perkin I, 1975, 1009].

Indeed, we have found that the presence of an organic acid of $pk_a$(dissociation constant defined at room temperature in an aqueous medium) of about 7 to 9 is essential to achieve satisfactory yields of the final products.

A further object of the present invention is accordingly a process for the preparation of γ,δ-unsaturated carboxylate esters of formula

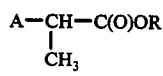 (Ia)

wherein symbol A represents a univalent radical of formula

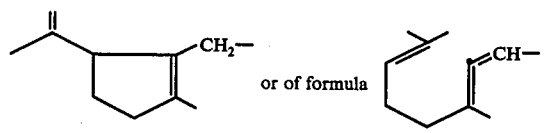

and symbol R represents a lower alkyl radical comprising from 1 to 6 carbon atoms, which comprises treating an α,β-unsaturated alcohol of formula

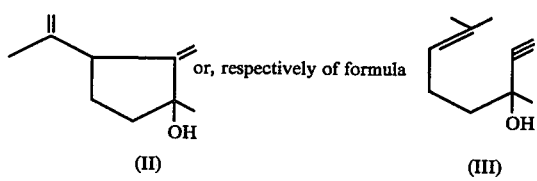

with a trialkyl ortho-propionate in the presence of an organic acid having a pk$_a$ of about 7 to 9.

According to an embodiment of the invention triethyl ortho-propionate is the preferred reactant. This compound is in fact commercially available or alternatively it can be easily synthesized according to known methods — see e.g.: Beilstein 2, 240 or German Pat. No. 1,192,180.

Preferential organic acids include more particularly phenol derivatives such as, e.g., o-nitrophenol, m-nitrophenol, p-nitrophenol, o-chlorophenol, m-chlorophenol and o-hydroxyacetophenone. o-Nitrophenol is preferred.

We have observed that by using the aforementioned acidic catalyst, the quantity of trialkyl ortho-propionate required for carrying out the addition reaction was much smaller than that suggested for analogous cases in the literature [see particularly: J. Amer. Chem. Soc., op.cit.], making the process of the invention even more attractive from the point of view of the overall economy.

The proportions of the ortho-ester used in accordance with the processes of the invention can vary however within a wide range, preferably between about 2 and 4 equivalents of said ortho-ester for each equivalent of α,β-unsaturated alcohol (II) or (III).

Although the best yields of carboxylates (Ia) were achieved by using concentrations at values comprised in the higher limits of the above given range, at concentrations beyond the above given upper limits the addition reaction is often accompanied by concomitant undesirable decomposition of the ortho-ester itself.

The temperature at which the addition reaction is effected can vary widely. For practical reasons the said reaction is carried out at a temperature of about the boiling point of the reaction mixture considered, preferably at a temperature slightly lower than the said boiling point. Thus, when triethyl ortho-propionate is used, good yields of end-products are achieved by operating at about 140° C, at which temperature the ethanol formed in the course of the reaction can be progressively collected.

It would be appreciated by those skilled in the art that the above indications, directed to the process for the preparation of γ,δ-unsaturated carboxylate esters of formula (Ia), also apply to the first reaction steps, (a) and respectively (i), in the processes of the invention for the preparation of the carboxylates of formula (I).

The following reaction steps (b) and (c), and respectively (ii) through (iv) are effected according to usual techniques.

Thus, for example, the reduction of the esters obtained in accordance with steps (a) or alternatively (i), is carried out by means of lithium aluminium hydride in diethyl ether, or by means of NaAl(C$_2$H$_5$)$_2$H$_2$ (OMH, available from Ethyl Corporation, Baton Rouge, La 70801, USA) in toluene.

Step (iii) is effected according to a method analogous to that described in German Pat. Nos. 1,082,257 and 1,193,490. Thus the cyclization of the allenic alcohol obtained sub letter (ii) is carried out at high temperature, comprised between about 250° and 500° C, preferably at between about 350° and 450° C at subatmospheric pressure and in an atmosphere of inert gas, such as nitrogen or argon.

The esterification steps, (c) or (iv), are effected by the usual means, for instance by preferentially treating the alcohol under consideration with mixed formic-acetic anhydride, or simply acetic anhydride, or with an acyl chloride such as acetyl chloride.

As previously indicated, steps (iii') and (iv') constitute together a variante of one of the processes of the invention. Though, this variation possesses an indeniable industrial interest, in much the same extent as the main process defined by reaction pathway (i) through (iv), it does not enable to achieve as high yields of end-products as those obtained by said main process. Probably, this is due to a competitive intramolecular elimination reaction on the allenic carboxylate used as starting material in step (iii'), as it will be apparent by the following scheme:

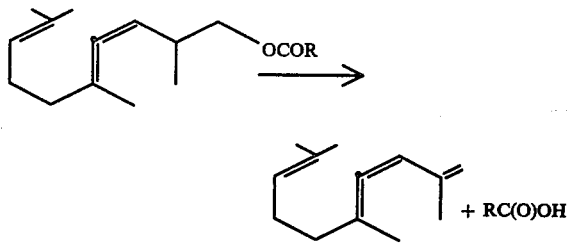

R = lower alkyl radical

The invention is better illustrated by but not limited to the following examples wherein the temperatures are indicated in degrees centigrade and the abbreviations have the meaning common in the art.

EXAMPLE 1

2-Methyl-3-[2-methyl-5-isopropenyl-cyclopent-1-en-1-yl]-propyl acetate (a) A mixture of 6.08 g (40 mM) of 1-methyl-2-methylene-3-isopropenyl-cyclopentanol, 14.0 g of triethyl ortho-propionate (80 mM) and 0.850 g of o-nitrophenol was heated at 140° during 6 h under argon atmosphere. Ethanol as well as a small amount of ethyl propionate were collected by distillation through a distillation column heated at about 80°. After elimination of the excess of triethyl propionate, the obtained residue has been taken up with ether, whereupon o-nitrophenol was eliminated from the ethereal phase by successively washing it with several portions of 5% aqueous sodium hydroxide. The usual working up consisting in drying the ethereal layers over MgSO$_4$, evaporation and distillation gave 5.50 g of a stereoisomeric mixture of ethyl 2-methyl-3-[2-methyl-5-isopropenyl-cyclopent-1-en-1-yl]-propionate: b.p. 120° – 130°/12 Torr; yield 58%. The obtained mixture had a purity of about 95%.

By operating in a way analogous to that described hereinabove, but by using 2.7 equivalents of triethyl orthopropionate (relative to starting cyclopentanol) the desired ester was obtained with an overall yield of 65%.

(b) A solution of 5.9 g (25 mM) of the ester, obtained according letter (a) above, in 13 ml of anyhydrous ether was added under stirring to a solution of 0.66 g (17.5 mM) of LiAlH$_4$ in 35 ml of anhydrous ether. The reaction mixture was kept under stirring and at reflux during 18 h, then, upon cooling, it was poured onto ice. After acidification with a 10% aqueous solution of HCl, extraction with ether, washing of the organic extracts with water and drying, the organic phase was evaporated and finally distilled to give 3.68 g of 2-methyl-3-[2-methyl-5-isopropenyl-cyclopent-1-en-1-yl]-propanol having b.p. 125°–7°/12 Torr; purity $\geq$ 95%.

(c) A mixture of 7.40 g (38 mM) of the alcohol obtained according to letter b) above, 6.70 g of acetic anhydride (66 mM) and 0.74 g of anhydrous sodium acetate was heated at 135° for 4 h, cooled then to room temperature and poured into 200 ml of water. This mixture was kept under stirring for 1 h in order to decompose the excess of acetic anhydride still present, whereupon it was extracted with diethyl ether.

The working up was effected by treating the mixture with an aqueous sodium bicarbonate solution and water, drying over MgSO$_4$ and distillation. 7.10 of a stereoisomeric mixture of 2-methyl-3-[2-methyl-5-isopropenyl-cyclopent-1-en-1-yl]-propyl acetate was thus obtained (yield 80%), purity $\geq$ 95%, b.p. 135°–8°/12 Torr. The analytical data of the obtained product were in all respects identical to those indicated in U.S. Pat. No. 3,937,723.

1-Methyl-2-methylene-3-isopropenyl-cyclopentanol, used as starting material in the process described above can be synthesized according to known methods — see German Pat. No. 1,082,257.

EXAMPLE 2

2-Methyl-3-[2-methyl-5-isopropenyl-cyclopent-1-en-1-yl]-propyl acetate (i) Ethyl 2,5,9-trimethyl-deca-3,4,8-trien-carboxylate 15.2 g (0.10 M) of 2,6-dimethyl-oct-2-en-7-yn-6-ol were mixed with 52.5 g (0.30 M) of triethyl ortho-propionate and 3.5 g (0.025 M) of ortho-nitrophenol and this mixture was heated at 140° for 4h. Ethanol, as well as a small amount of triethyl propionate were collected through a distillation column heated at about 85°. The following working up was effected as indicated sub letter (a) of Example 1 above.

A final distillation gave 19.5 g (0.083 M, yield 83%) of the desired ethyl carboxylate having b.p. 130°–135°/12 Torr in the form of a diastereoisomeric mixture.

NMR (60 MHz): 5.16 (2H, m); 4.12 (2H, q, J = 7 Hz); 3.03 (1H, m); 2.00 (3H, s, broad band); 1.8–2.8 (4H, m, complex band); 1.71 (3H, s); 1.66 (3H, s); 1.60 (3H, s); 1.24 (3H, t, J = 7.0 Hz); 1.27 (3H, d, J = 7.1 Hz) δ ppm;
IR (neat): 1730 and 1965 cm$^{-1}$;
MS: M$^+$ = 236 (16); m/e: 121 (100), 69 (93), 135 (88), 93 (85), 147 (83), 119 (78), 107 (75), 91 (46), 79 (45), 105 (43).

(ii) 2,5,9-Trimethyl-deca-3,4,8-trien-1-ol

A solution of 25 mM of the ester obtained according to letter (i) above in 13 ml of anhydrous ether was added under stirring to a solution of 0.66 (17.5 mM) of LiAlH$_4$ in 35 ml of anhydrous ether. Stirring was carried on at room temperature for 22 h, whereupon the reaction mixture was poured onto ice. After acidification with a 10% aqueous HCl solution, extraction with ether, washing with water and drying, followed by evaporation and distillation there was obtained a fraction having b.p. 130°–7°/12 Torr (yield 77%) containing 90–95% of the desired allenic alcohol in the form of a diastereoisomeric mixture.

NMR (60 MHz): 4.8–5.4 (2H, m badly resolved); 3.45 (2H, d, J = 6.1 Hz); 3.1–3.6 (1H, m); 2.00 (3H, s, broad band) 1.8–2.6 (4H, m, complex band); 1.70 (3H, s); 1.65 (3H, s); 1.60 (3H, s); 0.98 (3H, d, J = 6.1 Hz) δ ppm
IR: 3250, 1920 cm$^{-1}$;
MS: M$^+$ = 194 (5); m/e: 69 (100), 95 (94), 93 (76), 55 (72), 121 (66), 107 (57), 67 (54), 91 (49), 79 (49), 81 (37).

(iii)
2-Methyl-3-[2-methyl-5-isopropenyl-cyclopent-1-en-1-yl]-propanol 1.94 g of the allenic alcohol obtained according to letter (ii) above in 20 ml of pentane were added portionwise within 20 minutes into a thermolysis reactor constituted by a quartz tube filled with quartz rings. The tube was of 1 meter length and of 18 mm section. The thermolysis was carried out at 380° at about 100 Torr and in an argon atmosphere. The condensation of the vapours of pyrolysate was effected by external cooling with liquid nitrogen, whereupon a distillation of the said pyrolysate gave 1.56 g (yield about 80%) of the desired cyclic alcohol of a purity of about 90–95%. The analytical data of this product were identical to those indicated in U.S. Pat. No. 3,937,723.

(iv)
2-Methyl-3-[2-methyl-5-isopropenyl-cyclopent-1-en-1-yl]-propyl acetate

The cyclic alcohol obtained in accordance with letter (iii) above is converted into its corresponding acetate ester according to the same procedure as that described sub letter (c) in Example 1 above. The observed yield of the end-product was of about 90%, b.p. 135°–138°/12-Torr. (purity $\geq$ 95%).

What is claimed is:

1. A process for the preparation of an γ,δ-unsaturated carboxylate esters of formula

wherein symbol A represents a univalent radical of formula

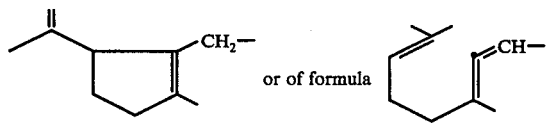 or of formula and symbol R represents a lower alkyl radical comprising 1 to 6 carbon atoms, which comprises:

reacting an α,β-unsaturated alcohol of formula

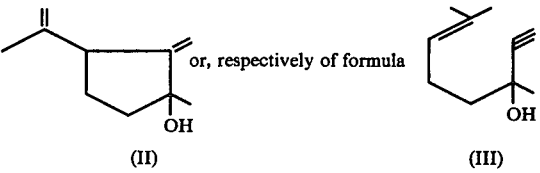

with a trialkyl ortho-propionate in the presence of an organic acid having a $pk_a$ of about 7 to 9.

2. A process according to claim 1 wherein the trialkyl ortho-propionate is triethyl ortho-propionate.

3. A process according to claim 1 wherein the organic acid is a phenol derivative.

4. A process according to claim 1 wherein the reaction is carried out at a temperature of about the boiling point of the reaction mixture.

* * * * *